United States Patent [19]

Wiley et al.

[11] Patent Number: 4,767,847

[45] Date of Patent: Aug. 30, 1988

[54] NOBAMYCIN ITS ANALOGS AND PROCESS THEREFORE

[75] Inventors: Paul F. Wiley; David W. Elrod, both of Kalamazoo, Mich.

[73] Assignee: The Upjohn Company, Kalamazoo, Mich.

[21] Appl. No.: 262,019

[22] Filed: May 11, 1981

Related U.S. Application Data

[63] Continuation of Ser. No. 60,326, Jul. 25, 1979, abandoned, which is a continuation-in-part of Ser. No. 32,614, Apr. 23, 1979, abandoned.

[51] Int. Cl.$^4$ .................... C07G 11/00; C07H 15/00; C07H 17/00; C07D 319/02
[52] U.S. Cl. .................................. 536/16.8; 549/358
[58] Field of Search .......................... 260/340.3, 349; 549/358; 536/17 A, 16.8

[56] References Cited

U.S. PATENT DOCUMENTS 4,064,340 12/1977 Wiley et al. ..................... 536/17 A
4,086,245 4/1978 Wiley et al. ..................... 549/358

OTHER PUBLICATIONS

Cram et al., Organic Chemistry, 2nd. Edition, pp. 272-274, McGraw-Hill (1964).
Tong et al., Abstracts of Papers, 175th ACS Meeting, Medicinal Division, paper 48.

*Primary Examiner*—Nicky Chan
*Attorney, Agent, or Firm*—Sidney B. Williams, Jr.

[57] ABSTRACT

The invention concerns a novel nogamycin having a heretofore unknown configuration and novel analogs which are active against various microorganisms. The invention also includes novel methods of making substituted and unsubstituted nogamycin having an essentially pure isomeric form of a preferred configuration.

21 Claims, No Drawings

NOBAMYCIN ITS ANALOGS AND PROCESS THEREFORE

CROSS REFERENCE TO RELATED APPLICATION

This application is a continuation of No. 060.326, filed Jul. 25, 1979, which is a continuation-in-part of application Ser. No. 32,614, filed on Apr. 23, 1979, both abandoned.

BACKGROUND OF THE INVENTION

The antibotic nogalamycin, and a process for its preparation, are described in U.S. Pat. No. 3,183,157. The structure of nogalamycin can be shown as follows:

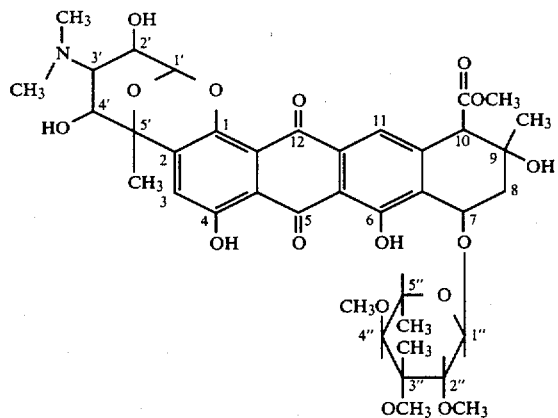

Antibotics nogalarol and nogalarene, produced by acid hydrolysis of nogalamycin, and O-methylnogalarol, produced by acidic methanolysis of nogalamycin or nogalarol, are disclosed in U.S. Pat. No. 3,501,569.

Nogalamycinic acid is prepared by chemical modification of nogalycimin. THe structure of nogalamycinic acid is as follows:

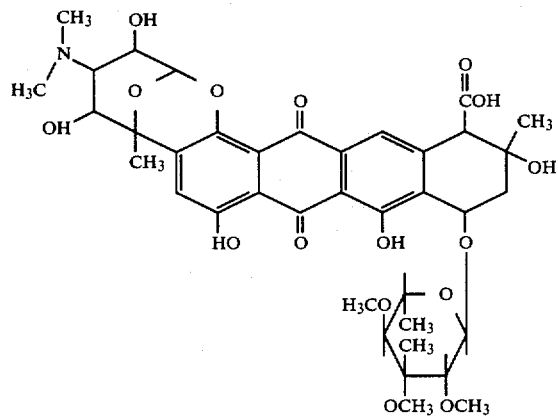

Nogalamycinic acid can be converted to nogamycin by contacting it with dimethylformamide (see U.S. Pat. No. 4,064,340). Nogamycin has the following structural formula:

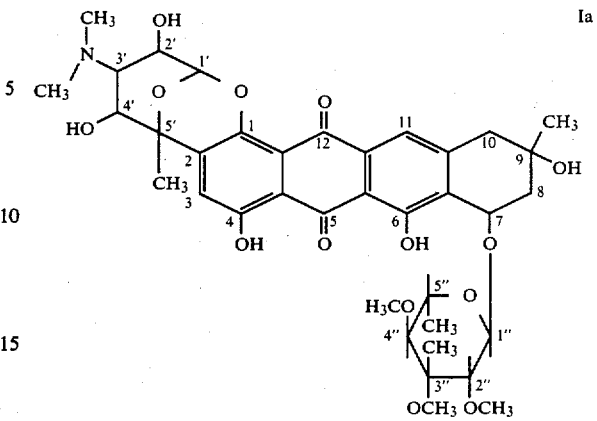

It is now found that the nogamycin prepared in the process of the above citation does not have the same structural formula as the nogamycin produced in the process of the instant invention.

U.S. Pat. No. 4,086,245 and U.S. application Ser. No. 924,975 concerns 7-1-alkylnogarols and their preparation from nogamycin.

Acid alcoholysis of nogamycins is the process used in the above preparations of 7-0-alkylnogarols having the following formulas:

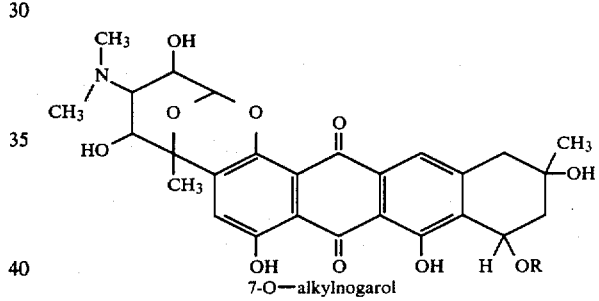

7-O—alkylnogarol wherein R is an alkyl group of from 1 to 4 carbon atoms, inclusive;

Additional prior art includes disclosure by Tong et al.; in Abstracts of Papers, 175th ACS meeting. Medicinal Division, paper 48, for a process which treats dauno:oethanethiol in trifluoroacetic acid mycinone with 2-aminoethanethiol in trifluoroacetic acid solution to obtain two diastereomers of a 7-(2-aminoethylthio) derivative.

Demonstrated advantageous biological use for the 7-0-alkylnogarols are included in U.S. Patent 4,086,245 and copending U.S. Ser. No. 924,975. Nogamycin itself has a demonstrated advantageous use in U.S. Pat. No. 4,064,340.

BRIEF SUMMARY OF THE INVENTION

Structurally novel nogamycin, as well as 7-nogarols and 7-deoxynogarols having various substituents at the 7 Position can be prepared according to a novel process of this invention such that an essentially pure stereoisomer having a preferred configuration results. Stereoisomers having the preferred configuration are advantageous because these exhibit superior anti-bacterial activity.

The essentially pure stereoisomers of the invention having the preferred configuration are such that the substituent that is not hydrogen at the 7 position and the hydroxyl group at the 9 position are either both above (α) or both below (β) the plane of the ring system to which they are attached. (Numbering of positions as used are noted above in Compound Ia). Since it is not now known whether the novel stereoisomers herein have a preferred configuration at the 7 and 9 positions which is α or β to the plane of the ring system, for ease of notation hereinafter the preferred configuration of the invention is expressed by the term "con" preceding the compound name.

The process mixes the nogamycin which is itself a novel compound of the present invention; the nogamycin which is prepared as described is U.S. Pat. No. 4,064,340: or a 7-0-alkylnogarol which is one of the 7-0-alkyl nogarols prepared in U.S. Pat. No. 4,086,245 and U.S. application Ser. No. 924,975, and haloacetic acid at −15° to 30° C. Nucleophiles are added either to the mixture or a solution of residue obtained by removing excess acid from the mixture. Nucleophilic substituents are thereby introduced at the C-7 position such that an essentially pure stereoisomer having the preferred configuration is obtained.

Additionally, novel 7-nogarols and novel 7-deoxynogarols having various substituents at the 7 position can now be prepared by the above process and therefore are also the subject of the present invention.

In addition to the above recited configuration of the invention the heterocyclic ring attached at the 1″ carbon of the nogamycin of the invention is in the beta position such that the 2″ carbon is below the 1″ carbon which is now found to have been unknown heretofore. In other words the nogamycin of the invention is more particularly con 1″βs-nogamycin.

DETAILED DESCRIPTION OF THE INVENTION

The present invention provides compounds having the following structural formulae:

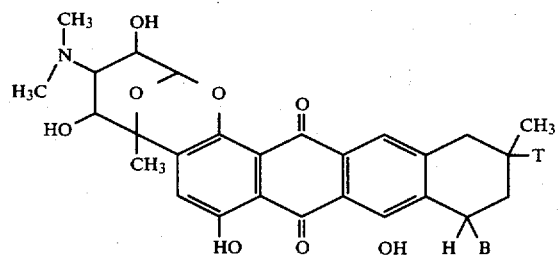

I wherein B is a nucleophile from a group comprising nogalosyl, a sulfide anion, organic acid anion, amino, substituted amino and carbanion, with the proviso that B is not -0—lower alkyl and T is hydroxyl such that B and T are attached to the ring system of I in the con configuration.

In the present invention, Formula I wherein B is nogalosyl means con 1″β-nogamycin now found to have been unknown heretofore. The formula for the novel con 1″β-nogamycin is as follows:

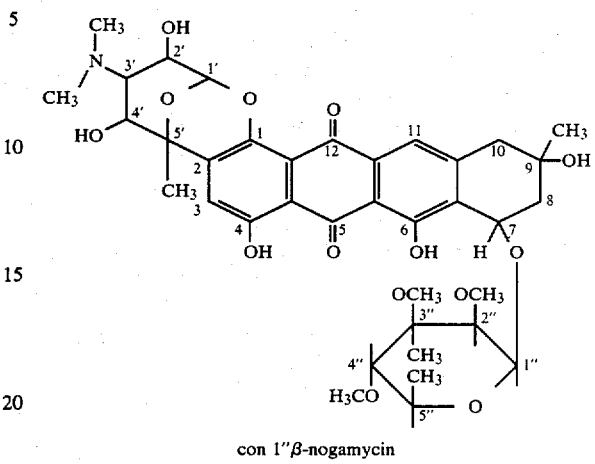

con 1″β-nogamycin (Note that 9-OH and 7-nogalosyl are required here to be either both above or both below the ring system of the nogamycin).

In addition to the compound I wherein B is nogalosyl, B further more specifically comprises alkylthioxy, acyloxy, amino, alkylamino, alkoxyalkylamino, aminoalkylalkoxy, and bis(carbalkoxy)methyl groups.

With respect to the alkylthioxy referred to above, there are included methylthioxy, ethylthioxy, n-propylthioxy, isopropylthioxy, n-butylthioxy, isobutylthioxy, and tertiarybutylthioxy moieties.

Acyloxy means acetoxy, n-propionyloxy, isopropionyloxy, n-butyryloxy, isobutyryloxy and tertiarybutyryloxy.

Bis(carbalkoxy)methyl means bis(carbomethoxy)methyl, bis(carbethoxy)methyl, bis(carbo-n-propoxy)methyl, bis(carboisopropoxy)methyl, bis(carbo-n-butoxy)methyl, bis(carboisobutoxy)methyl and bis(carbotertiarybutoxy)methyl.

Aminoalkylalkoxy means aminomethylmethoxy, aminoethylmethoxy, aminopropylmethoxy, aminobutylmethoxy, and and isomers thereof.

Alkylamino means methylamino, dimethylamino, ethyl amino, diethylamino, propylamino, butylamino and isomers thereof.

Alkoxyalkylamino means methoxypropylamino, methoxyethylamino, ethoxyethylamino, propoxyethylamino and isomers thereof.

The above named nucleophilic groups are not intended to be limiting since a wide range of novel compounds including con 1″β-nogamycin can be made by the process of the invention. Additionally, the process can be used to make the known 7-0-alkyl nogarols having the con configuration now thought to be disclosed in U.S. Pat. No. 4,086,245 essentially without forming another ismer thereof.

The process can be either a one or two step reaction as indicated below:

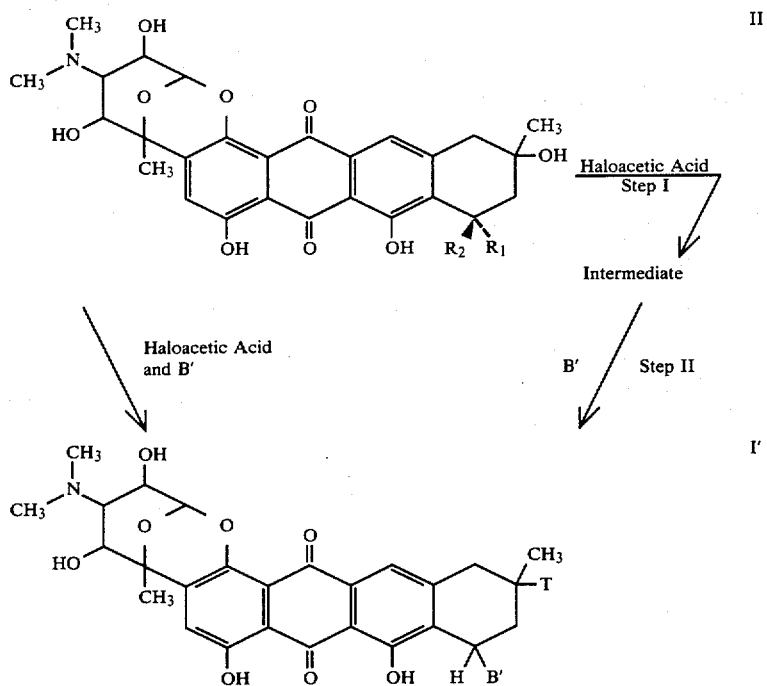

wherein R₁ and R₂ are selected from the group consisting of hydrogen, lower alkoxy, and nogalosyl such that one of R₁ and R₂ is always hydrogen, B' is a nucleophile, and T is hydroxyl such that B' and T are attached to the ring system in compound I' in the con configuration.

Nucleophile is meant to be non-limiting and subgenera named herein are only suggestions from a broad range of possible reacting groups known in the art to react because of the presence thereon of an unshared pair of electrons. In addition to specific groups such as nogalosyl, alkylthioxy, acyloxy, bis(carbalkoxy)methylaminoalkylalkoxy, and alkoxyalkylamino, comprising B above, it is suggested that B' also comprises alkoxy, aryloxy, aralkoxy, and the corresponding sulfoxy groups, as well as nitrogen moieties having the formula

The symbol

comprises an N-substituted heterocyclic group wherein R' and R" taken together with the nitrogen form the heterocyclic group such that R' and R" have up to two heteroatoms selected from the group consisting of nitrogen, sulfur and oxygen and wherein the heterocyclic group is a group having up to 7 carbon atoms.

The symbol $$-N\diagup^{R'}_{\diagdown R''}$$

also comprises an amino group wherein R' and R" selected from the group consisting of H, alkyl, alkenyl, cycloalkyl, cycloalkenyl, cycloalkalkyl, cycloalkenylalkyl, aryl, aralkyl, aralkenyl, aryloxyalkyl, heterocyclic, or heterocycloalkyl, wherein the heteroatoms are nitrogen, oxygen or sulfur having up to 10 carbon atoms apart from any substituents attached thereto, of which there may be one or two selected from hydroxy, carboxy, amino, lower alkoxy, benzyloxy, halogen, or lower alkyl.

When used herein the terms alkenyl are intended to include those containing up to four carbons such as ethylene, propylene, butylene and isomers thereof.

Haloacetic acid means mono, di and trifluoroacetic acid and mono, di and trichloroacetic acid.

The process contemplates a mixture of the haloacetic acid and a reactant selected from the group consisting of con 1's-nogamycin of the instant invention, nogamycin; in the configuration of the prior art as discussed above, and 7-0-alkylnogamycin to which a nucleophile is added. The mixture may also include an additional solvent. However, if for example, the halo acetic acid used is trifluoroacetic acid, an excess of trifluoroacetic acid may act as the solvent. The nucleophile may be reacted in a one step procedure. However, excess haloacetic acid and the additional solvent if present in the mixture may be reoved under pressure from the reaction mixture to leave a residue thought to be an intermediate (see Step I above).

The residue is dissolved for treatment with the nucleophile to obtain a product of the two step procedure. (see Step II above).

In either the one or two step procedure it is believed that the same intermediate forms between the nogamycin reactant and haloacetic acid. It is further believed that the intermediate is a complex and appears to exist in the mixture of the one step procedure or as the residue of Step I in the two step procedure. Efforts to characterize the intermediate are incomplete since it is relatively unstable. Speculation about the intervening intermediate herein is not meant to be limiting.

Solvents that may be used in the procedure include, for example, any solvent of the mixture of the nogamycin reactant and haloacetic acid such that the nucleophile reacts therein. Excess trifluoroacetic acid is most preferred. However, any itable solvent may be used such as tetrahydrofuran which is preferred and ether and dioxane.

The reaction proceeds at −15° to 30° C. for from ¼ to 6 hours.

The substituted 7-nogarols, 7-substituted-7-deoxynogarols and 1's-nogamycin having the preferred configuration previously described in the invention can be recovered by any method known in the art. For example, it may be precipitated in water in which the pH is adjusted between 7 and 7.2 and extracted with a suitable solvent, for example methylene chloride (preferred), chloroform, or ethyl acetate. Further, the product can be recovered from the extract by chromatography on silica gel using suitable solvent systems, for example, chloroform-methanol (95:5) and chloroform- methanol-water (78:20:2). A TLC of the product in the solvent system indicates homogeneous novel compounds having the above described configuration.

The novel con 1″β-nogamycin and nogamycin analogs of the present invention can be acylated under standard acylating conditions with an appropriate acid halide or anhydride to give the acylated compound. Such acylation can occur at one or more of the available hydroxyl groups.

The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric. caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentaecarboxylic acid, cyclopentenecarboxylic acid, methylcyclopentenecarboxylic acid, cyclohexanecarboxylic acid, diethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutyl berzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxyhydrocarbon carboxylic acids include hydrocarboncarboxylic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α-and β-chloropropionic acid;
α-and γ-bromobutyric acid;
α-and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecaboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentistic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethyl hydrogen carbonate);
and the like.

Acid addition salts of the novel compounds of the present invention can be made by neutralizing the compound with an appropriate acid to below about pH 7.0, and advantageously to about pH 2 to pH 6. Suitable acids for this purpose include tartaric, glucuronic, and lactic which give water soluble salts, and hydrochloric, sulfuric, phosphoric, sulfamic, hydrobromic, and the like which give relatively water insoluble salts.

Novel compounds of the invention or acylated and acid addition salts thereof, as described above, can be used as antibacterials.

The novel compounds of the invention and acid addition salts thereof inhibit the growth of microorganisms in various environments. For example, these compounds can be used for treating breeding places of silkworms, to prevent or minimize infections which are well known to be caused by *Bacillus subtilis*. Also the compounds are used to minimize or prevent odor in fish and fish crates caused by contamination with *B. subtilis*. Further, the compounds can be used to treat birds infected with *Mycobacterium avium*.

In addition, con-7-acetylnogarol, con-7-methylthio-7deoxynogarol, con-7-methylamino-7-deoxynogarol, con-7-di-methylamino-7-deoxynogarol, con-7- ethylamino-7-deoxynogarol, con-7-diethylamino-7-deoxynogarol, and con-7-azido-7-deoxynogarol have demonstrated antitumor activity against P388 leukemia cells in vivo in mice. Further, the above named con-7-amino compounds were strikingly less toxic than other connogamycin compounds.

The compounds and the acid salts described herein are used in the treatment of mammals, including man. For example, the compounds inhibit the growth of *Streotococcus pyogenes* known to cause infection in man.

The acylated compounds described above can be given to an animal possessing the necessary enzyme to remove the acyl group, thus freeing the parent antibiotic compound which then inhibits susceptible bacteria.

The compounds of the present invention are presented for administration to humans and animals in unit dosage forms, such as sterile parenteral solutions or suspensions, containing suitable quantities of compound of Formula I or acylated and acid addition salts thereof. Unit dosage forms may also be as tablets, capsules, pills, powders, granules, oral solutions or suspensions, and water-in-oil emulsions containing suitable quantities of compounds.

Dosage forms of the compound as discussed hereinafter refers to compounds of Formula I or acylated and acid addition salts thereof.

For oral aministration, either solid or fluid unit dosage forms can be prepared. For preparing solid composition such as tablets, the unit dosage is mixed with conventionl ingredients such as talc, magnesium stearate dicalcum phosphate, magnesium aluminum silicate, calcium sulfate, starch, lactose, acacia, methylcellulose, and functionall similar materials as pharmaceutical diluents or carriers. Capsules are prepared by mixing the compound with an inert pharmaceutical diluent and filling the mixture into a hard gelatin capsule of appropriate size. Soft geltin capsules are prepared by machine encapsulation of a slurry of the compound with an acceptable vegeable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroaloholic (ethanol) vehicle with suitable sweeteners such as sugar and saccharin together with an aromatic flavorng agent.

Suspensions can be prepared with an aqueous vehicle with the aid of a suspending agent such as acacia, tragacanth, metylcellulose and the like.

For parentral administration, which is preferred, fluid unit dosae forms are prepared utilizing the compound and as terile vehicle, water being preferred. The compound, dpending on the vehicle and concentration used, can be either suspended or dissolved in the vehicle. In preparing solutions the compound can be dissolved in water for injecion and filter sterilized before filling into a suitable vial or ampoule and sealing. Advantageously, adjuvants such as a local anesthetic, preservative and buffering agents can be dissolved in the vehicle. To enhance the stablity, the compositions can be frozen after filling ito the vial and the water removed under vacuum. The dry lyophilized powder is then sealed in the vial and an accmpanying vial of water for injection is supplied to reconstitute the liquid prior to use. Parenteral suspension can be prepared in substantially the same eral suspensionl manner except that the compound is suspended in the vehicle instead of being dissolved and sterilization cannot be accomplished by filtration. The compound can be sterilized by exposure to ethylene oxide before suspending in the sterile vehcle. Advantageously, a surfactant or wetting agent is included in the composition to facilitate uniform distribution of the compound.

The term "unit dosage form", as used in the specification, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are ampoules and vials, as well as tablets, capsules, pills, powder packets, wafers, granules, cachets, teaspoonfuls, tablesspoonfuls and dropperfuls, segregated multiples of the foregoing, and other forms as herein described.

An effective quantity of the compound is employed in treatment. The dosage of the compound for treatment depends on man factors that are well known to those skilled in the art. They include, for example, the route of administraton and the potency of the particular compound. A dosage schedule for humans of from about 500 to about 5000 mg. of compound in a single dose, administered parenterally are effective for treating bacterial infections. When intial dosages at the lower end of the above range are employed, the mammals progress is monitored and dosages on subsequent days are increased in the event that the patient or animal response is deemed by the attending physician or veterinarian to be absent or insufficient. The systemic toxicity of compounds of this invention must be carefully evaluated and subsequent dosages determined by evaluating the benefits of the drug in relationship to any such toxic manifestations.

The following examples are illustrative of the process and products of the invention, but are not tc be construed as limiing. All percentages are by weight and all solvent mixture proportions are by volume unless otherwise noted. All temperatures are in degrees Centigrade.

PREPARATION OF CON 1"β- NOGAMYCIN, 7-1-ALKYLNOGAROLS HAVING THE con CONFIGURATION AND NOVEL ANALOGS THEREOF

Example 1

Con 1"β-nogamycin.

A solution of 1 g (1.37 mmoles) of nogamycin is dissolved in 20 ml. of trifluoroacetic acid and the solution is cooled in an ice bath. A 53% suspension of 821 mg. of sodium hydride in mineral oil (18.1 mmoles) is washed with two 10-ml. portions of anhydrous tetrahydrofuran and added to 2 g. (9.1 mmoles) of nogalose in 30 ml. of anhydrous tetrahydrofuran. The mixture is stirred for 1 hour at room temperature and to it is added the cold trifluoroacetic acid soution. The reaction mixture is adjusted to pH 7.1 with 1 Nhydrochloric acid and diluted with 100 ml. of water. The aqueous solution is extracted with four 100-ml. portions of methylene chloride. The combined extracts are evaporated under reduced pressure to a red syrup. The residue is dissolved in a little methylene chloride and a large volume of Skellysolve B is added. The ppt is removed by filtration (yield 1.52 g.), and the filtrate is evaporated under reduced pressure. The residue is chromatographed on a short column of 20 g. of silica gel using methylene chloride-methanol (19:) and collecting the colored fractions and evaporating. The residue is dissolved in a small amount of methylene chloride, and the solute is pptd with Skellysolve B.

The precipitates are combined and chromatographed by HPLC using 60 g of silica gel and the solvent system methylene chloride-methanol (96:4) and collecting 10-ml. fractions. The solvent is then changed to 93:7 and a total of 105 fractions are collected. Those fractions (51–105) are combined which, as judged by TLC with chloroform-methanol-water(78:20:2; $R_f$ 0.53) contained only con 1"β-nogamycin. The combined fractions are evaporated to dryness under reduced pressure, yield 325 mg. This material is chromatographed on 2-mm preparative thick-layer plates using chloroform-methanol-water (78:20:2). The appropriate band is removed and extracted with methylene chloride-methanol. There is obtained 185 mg of con 1"β-Nogamycin, mp 217°–219° dec;$[\alpha]_D$+596° (c 0.147, CHCl$_3$); UV (C$_2$H$_5$OH) 236 nm (ε51,600), 258 (ε24,200), 292 sh (ε9,750), 478 (ε15,300); IR (nujol) 3440, 1660, 1610, 1580, 1410, 1280, 1210, 1090, 1050, 990, 930, 910, 880, 850, 820, 770, 720, and 690 cm−1; $1_H$ NMR (CDCl$_3$)δ1.23, 1.46, 1.74 (s, m, s, 12 H, CH$_3$C), 2.61 [s, 6 H, (CH$_3$)$_2$N], 3.26, 3.42, 3.55 (3 s, 9 , CH$_3$O), 2.0–2.2, 3.1–4.2 (m, CHO and CHN), 5.03 (m, 1 H, H-7), 5.23 (d, 1 H, H-1"), 5.90 (d, 1 H, H-1'), 6.60 (s, 1 H, H-3), 7.25 s, 1 H, H-11); 13$_C$ NMR (CDCl$_3$) δ190.9 (C-5), 179.4 (C-12), 161.2 (C-6), 155.6 (C-4), 148.3 (C-1), 147.0 (C-10a), 137.9 (C-2), 132.7 (C-11a), 129.6 (C-6a), 125.6 (C-3), 120.8 (C-11), 116.1 (C-12a), 114.4 (C-4a), 112.5 (C-5a), 102.2 (C-1"), 97.6 (C-1'), 84.3 (C-4"), 81.5 (C-2"), 79.0 (C-3"), 75.1 (C-5 ), 72.7 (C-2'), 71.0 (C-4'), 70.8 (C-7), 70.4 (C-5"), 67.6 (C-9), 66.1 (C-3'), 61.4, 61.2, 48.2 (3 CH$_3$O), 43.9 (C-10), 41.6 [(CH$_3$)$_2$N], 40.2 (C-8), 30.5 (C-9 CH$_3$), 24.0 (C-5' CH$_3$), 18.5 (C-5" CH$_3$), 15.3 (C-5' CH$_3$); mass spectrum m/e 729.3011 (Calcd for C$_{37}$H$_{47}$NO$_{14}$, 729.2997).

Anal. Calcd. for C$_{37}$H$_{47}$NO$_{14}$:
C, 60.90; H, 6.49; N, 1.92.
Found: C, 59.09; H, 6.39; N. 1.83.

Example 2

Con 7-O-methylnogarol

A Solution of 1 g. of nogamycin in 20 ml. of trifluoroacetic acid is cooled in an ice bath and stirred for 5 hours. Stirring is continued while a solution of sodium methoxide in methanol is added dropwise until the reaction mixture turns purple. One hundred ml. of water is added, the pH is adjusted to 7.0 with additional sodium methoxide, and the mixture is extracted with three 100-ml. portions of methylene chloride. The combined extracts are evaporated to dryness under reduced pressure, wt. 1.004 g. A mixture of 0.5 g. of residue, 15 ml. of 0.1 M glucuronic acid, 10 ml. water, and 10 ml. of methanol is stirred for 15 minutes and filtered. The filtrate is neutralized (pH 7.0) with 1 N sodium hydroxide and stirred while maintaining at pH 7. After about 30 minutes the precipitate is collected by filtration, yield 211 mg. of con 7-0-methylnogarol. TLC in chloroform-methanol-water (78:20:2) indicates the material is homogeneous and identical with the same material prepared by methanolysis: $[\alpha]_D$ 897° (c 0.1525, CHCl$_3$); $^{13}$C NMR identical with that of previously prepared material; mass spectrum m/e 541.

Anal. Found: C, 61,65; H, 5.82; N, 2.56.

Example 3

Conversion of con 7-0-Methylnogarol to con 7-0ethylnogarol

A solution of 200 mg. of con 7-0-methylnogarol in 2 ml. of trifluoroacetic acid is allowed to stand at room temperature for ¼ hour. While the reaction mixture is stirred a solution of sodium ethoxide in ethanol is added slowly until the mixture turns purple. The reaction mixture is poured into 50 ml. of water, and the solution is adjusted to pH 7.2 with 1 N HCl. The aqueous mixture is extracted with three 50-ml. portions of methylene chloride. The combined extracts are dried (sodium sulfate) and evaporated under reduced pressure to give a residue which is washed with Skellysolve B, yield 202 mg. This is purified by preparative TLC using a 2-mm silica gel plate and the solvent system chloroform-methanol-water (78:20:2). The faster moving portion is removed and extracted with chloroform-methanol (9:1) as one fraction and the slower moving portion as a second fraction. The first fraction gives 94 mg. of material having the same $R_f$ as con 7-0-ethylnogarol in the above solvent system. The product is further identified as con 7-0-ethylnogarol by a mass spectrum (M/E) 555) and $1_h$ NMR.

Example 4

Con 7-Methylthio-7-deoxynogarol

A solution of 0.5 g of nogamycin in 10 ml. of trifluoroacetic acid is allowed to stand at room temperature for 1 1/4 hour. The solution is evaporated to dryness under reduced pressure, and 15 ml. of dry tetrahydrofuran is added. The solution is cooled and a slight excess of hydrated sodium methylmercaptide is added. The mixture is stirred at 0° or 1 hour. After removal of the solvent by evaporation under reduced pressure, the residue is dissolved in 100 ml. of water. The pH is adjusted to 7.8 with 1 N hydro-hloric acid, and the solution is extracted with two 50-ml portions of chloroform. The combined extracts are evaporated under reduced pressure to give a residue which is chromatographed on 30 g. of silica gel using chloroform-methanol (95:5) and collecting 10-ml. fractions. Fractions 34–69 are combined on the basis of TLC in chloroform-methanol-water (78:20:2; $R_f$ 0.56) and evaporated under reduced pressure to give 204 mg. of con 7-methylthio-7-deoxynogarol (yield 53%): $[\alpha]_D$+719° (c, 0.115, CHCl$_3$)237 nm (ε48,100), 262 (ε23,250), 280 sh (ε10,800), 479 (ε16,050); IR (njuol) 3440, 1660, 1620, 1575, 1285, 1245, 1220, 1105, 1055, and 1005 cm−1; $1_H$ NMR (CDCl$_3$)δ1.48 (s, 3 H, CH$_3$C), 1.74 (S, 3 H, CH$_3$C), 2.38 (s, 3H, CH$_3$S), 2.57 [s, 6 H, (CH$_3$)$_2$N], 2,81 (m), 3.53 (m, 1H, CHO), 3.69 (m, 1 H, CHO), 4.38 (m, 1 H, H-7), 5.95 (d, 1 H, H-1'), 6.59 (s, 1 H, H-3), 7.30 (s, 1 H, H-11); 13$_C$NMR (CDCl$_3$) δ191.1 (C-5), 179.7 (C-12), 160.3 (C-6), 155.7 (C-4), 148.2 (C-1), 146.1 (C-10a), 137.7 (C-2), 132.1 (C-11a), 130.3 (C-6a), 125.5 (C-3), 120.6 (C-11), 114.4 (C-12a), 112.5 (C-4a) , 110.2 (C-5a), 97.6 (C-1'), 75.1 (C-5'), 72.7 (C-2'), 70.5(C-4'), 68.7 (C-9), 66 (C-3'), 43.9 (C-10)

41.6 [(CH$_3$)$_2$N], 38.5 (C-7), 36.9 (C-8) 31.2 (C-9 CH$_3$), 23.9 (C-5' CH$_3$), 16.5 (CH$_3$S) mass spectrum m/e 557.
Anal. Calcd. for C$_{28}$H$_{31}$NO$_9$S:
C. 60.36; H, 5.60; N, 2.52; S, 5.75.
Found: C, 58.75; H, 5.60; N, 2.98; S, 5.44.

Example 5

Con 7-0-acetylnogaizol

A solution of 1 g. of nogamycin in 25 ml. of trifluoroacetic acid is stirred at room temperature for 1 1/2 hour. The excess trifluoroacetic acid is removed under reduced pressure, and the residue is dissolved in 100 ml. of anhydrous terahydrofuran. Three g. of anhydrous sodium acetate is added, and the mixture is stirred for 68 hours. The solvent is removed by evaporation under reduced pressure, and the residue is dissolved in 100 ml. of water. The queous solution is adjusted to pH 7 and extracted with three 35-ml. portions of chloroform. The combined chloroform extracts is evaporated under reduced pressure, and the residue is chromatographed on 30 g. of silica gel using chloroform-methanol (9:1) and collecting 10 ml. fractions. On the basis of TLC (chloroform-methanol-water; 78:20:2; Rf 0.48) fractions 23–34 are combined. The cmbined fractions are evaporated under reduced pressure to give 71 mg. of con 7-0-acetylnogarol [α]$_D$+674° (c 0.1995, CHCl$_3$); UV (C$_2$H$_5$OH) 236 nm (ε40,150), 259 (ε21,250), 289 sh (ε8,550), 478 (ε13,150); $^1H$ NMR (CDCl$_3$)δ1.45 (s,3 H, CH$_3$C), 1.73 (s, 3 H, CH$_3$C), 2.05 (s, 3 H, CH$_3$CO), 2.2–3(m, CH$_2$ and CHN), 2.62 [s, OH, (CH$_3$)$_2$N], 3.1–3.8 (m, CHO), 4.23 (m, 1 H, H-7), 5.93.(d, 1 H, H-1'), 6.62 (s, 1 H, H-3), 7.23 (s, 1H, H-11); $^{13}$C NMR (CDCl$_3$)δ190.8 (C-5), 179.5 (C-12), 169.3 CH$_3$CO), 161.2 (C-6), 155.7 (C-4), 148.2 (C-1), 146.7 (C-10a), 137.7 (C-2), 133.2 (C-11a), 127.3 (C-6a), 125.7 (C-3), 120.2 (C-11), 115.8 (C-12a), 113.9 (C-4a), 112.8 (C-5a), 97.5 (C-1'), 75.1 (C-5'), 72.6 (C-2'), 70.3 (C-4'), 67.6 (C-9), 66.2 (C-3'), 63.9 (C-7), 43.6 (C-10), 41.6 (CH$_3$)$_2$N], 35.7 (C-8), 29.3 (C-9 CH$_3$), 24.0 (C-5'CH$_3$), 21.0 (CH$_3$CO); mass spectrum m/e 511 (M+—CH$_3$COOH).

Example 6

Con 7-Bis(carbethoxy)methyl-7-deoxynogarol

A solution of 250 mg. of nogamycin in 5 ml, of trifluoroacetic acid is allowed to stand for 1-1/2 hours, and the acid is removed by evaporation under reduced pressure. The residue is dissolved in 10 ml. of anhydrous tetrahydrofuran and added dropwise to a slurry prepared by adding 0.5 g. of sodium hydride as a 53% suspension in mineral oil and 1.5 ml. of diethyl malonate to 40 ml. of anhydrous tetrahydrofuran cooling to 0°. After 15 minutes the reaction mixture is adjusted to pH 7 with 1 N hydrochloric acid and concentrated under reduced pressure. Water (25 ml.) is added, and the mixture is extracted with three 15- ml. portions of chloroform. The combined extracts are evaporated to dryness under reduced pressure, and the residue is chromatographed on 10 g. of silica gel using chloroform-methanol (95:5) and collecting 5-ml. fractions. On the basis of TLC (chloroform-methanol-water; 78:20:2; Rf 0.42) fractions 14–26 are combined. Evaporation under reduced pressure gives 50 mg. of material which is rechromatographed on 2-mm thick-layer plates using acetonemethanol (9:1) to yield con 7-bis(carbethoxy)methyl-7deoxynogarol. This product is homogeneous by TLC in the above system; $^1$H NMR (CDCl$_3$)δ1.10 (t, 3 H, CH$_3$CH$_2$), 1.33 (t, 3 H, CH$_3$CH$_2$), 1.45 (s, 3 H, CH$_3$C), 1.70 (s, 3 H, CH$_3$C), 2.46 [s, 6 H, (CH$_3$)$_2$N], 2.20–4.40(m, CH$_2$, CH$_2$O, CHO, CHN), 4.80 (d, 1 H,

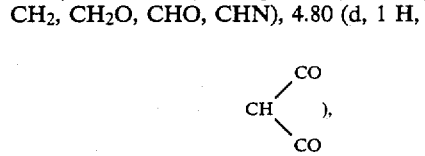

5.08 (d, 1 H, H-1'), 7.10 (s, 1 H, H-3), 7.15 (s, 1 H, H-11).

Example 7

Con 7-(2-methoxyethylamino)-7-deoxynogarol

A solution of 500 mg. of nogamycin in 5 ml. of trifluoroacetic acid is allowed to stand at room temperature for 2 hours and the excess acid is removed by evaporation under reduced pressure. The residue is dissolved in 25 ml. of anhydrous tetrahydrofuran, and 2-methoxyethylamine is added dropwise until the solution became purple. It is adjusted to pH 7.2 with 1 N hydrochloric acid, 50 ml. of water is added, and the mixture is extracted with three 50-ml. portions of methylene chloride. The combined extracts are concentrated to dryness under reduced pressure leaving an oily residue which is washed with Skellysolve B, yield 288 mg. The ppt is dissolved in 25 ml. of tetrahydrofuran, dry hydrogen chloride is bubbled in until a ppt is obtained which is removed by filtration. This material is crystallized from methanol-acetone obtaining two crops which are combined. This material is dissolved in water, and the solution is first adjusted to pH 9 (0.1 N sodium hydroxide) then to 8 with 0.1 N HCl. It is then extracted with methylene chloride keeping the pH at 8 by additions of base. The combined extracts are dried (sodium sulfate) and evaporated under reduced pressure to give 107 mg. of con 7-(2-methoxyethylamino)-7-deoxy-nogarol which is homogeneous by TLC in chloroform-methanolwater (78:20:2; R$_f$0.50). IR (nujol) 3310, 1665, 1615, 1580, 1565, 1450, 1405, 1370, 1280, 1210, 1095, 1040, 995, 905, 875, 850, 830, 770, and 715 cm−1; $^1$H NMR (CDCl$_3$)δ1.43 (s,3 H, CH$_3$C), 1.75 (s, 3 H, CH$_3$), 2.57 [s, 6 H, (CH$_3$)$_2$N], 3.33 (s, 3 H, CH$_3$O), 2.15–3.55 CH$_2$, CH$_2$O, CH$_2$N, CHO, CHN , 4.33 (m, 1 H, H-7), 6.00 (d, 1 H, H-1'), 6.58 (s, 1 H, H-3), 7.30 (s, 1 H, H-11); $^{13}$C NMR (CDCL$_3$)δ191.0 (C-5), 179.4 (C-12), 160.1 (C-6), 155.7 (C-4), 148.4 (C-1), 147.3 (C-10a), 137.8 (C-2), 132.2 (C-11a), 131.4 (C-6a), 125.6 (C-3), 120.9 (C-11), 116.0 (C-12a), 114.4 (C-4a), 112.4 (C-5a), 97.7 (C-1'), 75.1 (C-5'), 72.7 (C-2'), 71.6 (CH$_2$O), 70.6 (C-4'), 68.1 (C-9), 66.0 (C-3'), 58.8 (2 CH$_3$O), 50.6 (C-7), 47.1 (CH$_2$N), 44.6 (C-10), 41.6 [(CH$_3$)$_2$N], 34.3 (C-8), 30.5 (C-9 CH$_3$), 23.8 (C-5'CH$_3$).

Example 8

Con-7-Ethylamino-7-deoxynogarol

A solution of 1 g of disnogamycin in 5 ml of trifluoroacetic acid is stirred at room temperature for 2½ hours. The mixture is evaporated to dryness under reduced pressure. The residue is dissolved in 20 ml of anhydrous tetrahydrofuron, and the solution is cooled in an ice bath while ethylamine is bubbled in until the reaction mixture is purple. The mixture is evaporated to dryness under reduced pressure followed by solution of the residue in anhydrous tetrahydrofuran. Dry hydrogen chloride is bubbled into the mixture until it is in excess. The orange precipitate is removed and recrystallized from methanolacetone. The product is dissolved in 60 ml of water, the aqueous solution is adjusted to pH 8.0 with 1 N sodium hydroxide, and the product is extracted with four 20-ml portions of chloroform-methanol (9:1). The combined extracts are dried over sodium sulfate, filtered, and evaporated under reduced pressure to yield 383 mg of con-7-ethylamino-7-deoxynogarol: $R_f$ 0.10 (SiO$_2$; CHCl$_3$-CH$_3$OH$_2$O; 78:20:2); UV (EtOH) λmax 234 (ε29,406), 249sh (λ23,366), 259sh (ε18,119), 268sh (ε15,248), 290sh (ε9,406), 478 (ε11,980); IR (Nujol) 3375, 1665, 1510, 1590, 1575, 1290, 1225, 1170, 1120, 1060, 1010, 945, 920, 890, 845, 785, and 710 cm−1; 13C NMR (CDCl$_3$+CD$_3$OD) δ190. 8 (C-5), 179.6 (C-12), 159.9 (C-6), 155.6 (C-4), 148.2 (C-1), 147.0 (C-20a), 137.7 (C-2), 132.3 (C-11a), 131.3 (C-6a), 125.5 (C-3), 120.8 (C-11), 116.0 (C-12a), 114.4 (C-4a), 112.4 (C-5a), 97.6 (C-1'), 75.2 (C-5'), 72.8 (C-2'), 70.6 (C-4'), 68.4 (C-9), 66.0 (C-3'), 50-6 (C-7), 44.4 (C-10), 42.0 (CH$_2$NH), 41.6 [(CH$_3$)$_2$N], 34.2 (C-8), 30.3 (C-9 CH$_3$), 23.8 (C-5' CH$_3$), 14.9 (CH$_3$CH$_2$).

Example 9

Con-7-Methylamino-7-deoxynogarol

A solution of 500 mg of disnogamycin in 5 ml of trifluoroacetic acid is stirred at room temperature for 2 hours. The solution is evaporated under reduced pressure, and the residue is dissolved in 10 ml of anhydrous tetrahydrofuran. The solution is cooled in an ice bath, and methylamine is bubbled into it until the reaction mixture is purple. The mixture is evaporated under reduced pressure. The residue is dissolved in 10 ml of tetrahydrofuran, and 50 ml of water is added. The pH is 8.0. The aqueous mixture is extracted with five 50-ml portions of methylene chloride which are combined and dried over sodium sulfate. The dried solution is filtered and evaporated to dryness under reduced pressure. The residue is dissolved in 10 ml of methylene chloride, and 150 ml of Skellysolve B is added. The collected precipitate weighs 241 mg. This material is dissolved in 25 ml of tetrahydrofuran, and dry hydrogen chloride is bubbled in until it is in excess. The resulting precipitate is collected and recrystallized from methanol-tetrahydrofuran to yield (2 crops) 204 mg. The salt is dissolved in 30 ml of water, and the pH is adjusted to 8.0 with dilute sodium hydroxide. The aqueous mixture is extracted with four 50-ml portions of methylene chloride. The combined extracts are dried over sodium sulfate, filtered, and evaporated in vacuo to yield 85 mg of con-7-methylamino-7-deoxynogarol: $R_f$ 0.12 (SiO$_2$; ChCl$_3$-CH$_3$OH-H$_2$O; 78:20:2); UV (EtOH); λmax 235 nm (ε34,225), 248sh (ε20,820), 258sh (ε18,139), 290sh (ε9,621), 480 (ε12,050); IR (Nujol) 3390, 1670, 1625, 1595, 1585, 1305, 1225, 1105, 1050, 1005, 945, 920, 890, 830, 780, and 725 cm−1; 13C NMR (CDCl$_3$+CD$_3$OD) δ191.0 (C-5), 179.5 (C-12), 160.0 (C-6), 155.7. (C-4), 148.3 (C-1), 147.2 (C-10a), 137.9 (C-2), 132.4 (C-11a), 131.3 (C-6a), 125.6 (C-3), 120.9 (C-11), 116.0 (C-12a), 114.3 (C-4a), 112.4 (C-5a), 97.6 (C-1'), 75.1 (C-5'), 72.8 (C-2'), 70.6 (C-4'), 68.4 (C-9), 66.0 (C-3'), 52.5 (C-7), 44.5 (C-10), 41.6 [(CH$_3$)$_2$N], 34.3 (CH$_3$-NH), 33.6 (C-8), 30.4 (C-9 CH$_3$), 23.9 (C-5'CH$_3$).

Example 10

Con-7-Dimethylamino-7-deoxynogarol

This is run as the preceding experiment but using dimethylamine instead of methylamine. The yield of con-7-dimethylamino-7-deoxynogarol is 146 mg: $R_f$0.21 (Si02; CHCl$_3$-CH$_3$OH-H$_2$O(78:20:2); UV (EtOH) λmax 237 nm (ε27,530), (ε248sh (20,260), 260sh (ε14,740), 270sh (ε13,149), 289sh (ε8,474), 478 (ε10,065); IR (Nujol) 3375, 1655, 1615, 1585, 1290, 1220, 1100, 1050, 1005, 920, 840, 780, and 735 cm−1; 13C NMR (CDCl$_3$+CD$_3$OD) δ190.6 (C-5), 180.0 (C-12), 161.6 (C-6), 155.6 (C-4), 143.0 (C-1), 147.6 (C-10a), 137.4 (C-2), 132.8 (C-11a). 129.6 (C-6a), 125.5 (C-3), 120.4 (C-11), 116.2 (C-12a), 114.7 (C-4a), 112.5 (C-5a), 97.5 (C-1'), 75.2 (C-5'), 72.8 (C-2'), 70.5 (C-4'), 68.6 (C-9), 66.0 (C-3'), 56.4 (C-7), 45.1 (C-10), 41.9 [(CH$_3$)$_2$N], 41.5 [(CH$_3$)$_2$N], 35.2 (C-8), 30.4 (C-9 CH$_3$), 23.9 (C-5'CH$_3$).

Example 11

Con-7-Diethylamino-7-deoxynogarol

This is done as the experiment making the methylamine analog except that 2 ml of diethylamine is added dropwise rather than bubbling in methylamine, yield of con-7-di ethylamino-7-deoxynogarol is 295 mg: Rf 0.14 (SiO$_2$; CHCl$_3$-CH$_3$OH-H$_2$O; 78:20:2); UV (EtOH) λmax 236 nm (ε31,156), 248sh (ε23,129), 259sh (ε17,925), 270sh (ε15,136), 290sh (ε9,184), 478 (ε11,361); IR (Nujol) 3375, 655, 1620, 1590, 1295, 1225, 1115, 1055, 1015, 925, 915, 835, and 790 cm−1; 1H NMR (CDCl$_3$+CD$_3$OD) δ1.00 (t, 3H, CH$_3$CH$_2$) 1.18 (t, 3H, CH$_3$CH$_2$) 1.40, 1.73 (2s, 6H, 2CH$_3$C), 2.54 [2, 6H, (CH$_3$)$_2$N], 2.75–4.50 (CHO, CHN), 5.52 (s, 1H, H-7), 5.92 (d, 1H, H-1'), 6.49 (1H, s, H-3), 7.13 (s, lH, H-11).

Example 12

Con-7-Azido-7-deoxynogarol

A solution of 1 g of disnogamycin in 10 ml of trifluoroacetic acid is stirred for 2½ hours at room temperature. The acid is removed by evaporation under reduced pressure, and the residue is dissolved in 30 ml of anhydrous acetone. Two grams of sodium azide is added and the mixture is stirred for 18 hours. The mixture is mixed with 100 ml of water, and the resulting mixture is adjusted to pH 7.3 with 5% sodium bicarbonate solution. It is then extracted with three 50-ml portions of methylene chloride. The combined extracts are concentrated under reduced pressure, and the residue is chromatographed on 100 g of silica gel using acetone-methylene chloridemethanol (75:15:10) and collecting 5-ml fractions. The fractions containing only the azide as determined by tlc using acetone-methanol-water (80:18:2) and chloroform- methanol-water (78:20:2) are combined and evaporated under reduced pressure, yield of con-7-azido-7-deoxynogarol is 242 mg (32%): $R_f$0.45 (SiO$_2$; CHCl$_3$-CH$_3$OH-H$_2$O; 78:20:2); UV (EtOH) λmax 236 nm (ε33,762), 258 (ε17,685), 287 (ε7,717), 476 (ε11,093); IR (Nujol) 3425, 2100, 1655, 1615, 1570, 1415, 1335, 1285, 1250, 1220, 1145, 1115, 1100, 1050, 1000, 965, 935, 915, 880, 835, 775, and 720 cm−1; 13C NMR (CDCl$_3$-CD$_3$OD) δ189.6 (C-5), 176.0 (C-12), 160.8 (C-6), 155.7 (C-4), 147.1 (C-1), 146.0 (C-10a), 137 (C-2), 133.1 (C-11a), 128.8 (C-6a), 125.8 (C-3), 120.4 (C-11), 115.1 (C-12a), 114.5 (C-4a), 112.0 (C-5a), 97.4 (C-1'), 75.3 (C-5'), 72.6 (C-2'), 70.2 (C-4'), 68.6 (C-9), 66.3 (C-3'), 55.6 (C-7), 43.9 (C-10), 42.1 (C-8), 41.6 [(CH$_3$)$_2$N], 29.8 (C-9 CH$_3$), 24.0 (C-5' CH$_3$); mass spectrum (FD) m/e 552 (Calcd. for C$_{27}$H$_{28}$N$_4$O$_9$, 552).

Utilizing a procedure similar to Example 2 above but substituting the appropriate sodium alkoxides, there are obtained con 7-0-alkyl nogarols as follows:
con 7-0-ethylnogarol,
con 7-0-n-propylnogarol,
con 7-0-isopropylnogarol,
con 7-0-n-butylnogarol, con 7-0-isobutylnogarol,
con 7-0-tertiarybutylnogarol.

Similarly substitution of the appropriate sodium alkoxide in a procedure such as that used in Example 3 the higher con 7-0-alkylnogarols, such as con 7-0-n-propylnogarol, con 7-0-isopropylnogarol, con 7-0-n-butylnogarol, con 7-0-isobutylnogarol and con 7-0-tertiarybutylnogarol, are obtained.

Further, substitution of the appropriate sodium aminoalkylalkoxide in a procedure such as either Example 2 or Example 3 makes con 7-0-aminoethylnogarol, con 7-0-amino-n-propylnogarol, con 7-0-aminoisopropylnogarol, con -0-amino-n-butylnogarol, con 7-0-aminoisobutylnogarol, con 7-0-aminotertiarybutylnogarol, having essentially the configuration of the invention as described herein.

Various additional con 7 analogs of nogamycin can be obtained by substituting related reactants such as the appropriate sodium alkylmercaptide, sodium acylate, dialkyl malonate, alkoxyalkylamine, ammonia and alkylamine for the nucleophilic reactant in a procedure similar to each of examples 4, 5, 6, 7, and 8 above to obtain the following compounds:
con 7-ethylthio-7-deoxynogarol,
con 7-n-propylthio-7-deoxynogarol.
con 7-isopropylthio-7-deoxynogarol,
con 7-n-butylthio-7-deoxynogarol,
7-isobutylthio-7-deoxynogarol,
con 7-tertiarybutylthio-7-deoxynogarol,
con 7-0-n-propionylnogarol,
con 7-0-isopropionylnogarol,
con 7-0-n-butyrylnogarol,
con 7-0-isobutyrylnogarol,
con 7-0-tertiarybutyrylnogarol,
con 7-bis(carbo-n-propoxy)methyl-7-deoxynogarol,
con 7-bis(carboisopropoxy)methyl-7-deoxynogarol,
con 7-bis(carbo-n-butyryl)methyl-7-deoxynogarol,
con 7-bis(carboisobutyryl)methyl-7-deoxynogarol,
con 7-bis(carbotertiarybutyryl)methyl-7-deoxynogarol,
con 7-methoxypropylamino-7-deoxynogarol,
con 7-methoxyisopropylamino-7-deoxynogarol,
con 7-ethoxyethlamino-7-deoxynogarol,
con 7-propoxyethylamino-7-deoxynogarol,
con 7-isopropoxyethylamino-7-deoxynogarol,
con 7-amino-7-deoxynogarol,
con 7-n-propylamino-7-deoxynogarol,
con 7-isiopropylamino-7-deoxynogarol,
con 7-n-butylamino-7-deoxynogarol,
con 7-isobutylamino-7-deoxynogarol,
con 7-tertiarybutylamino-7-deoxynogarol.

Other novel substituted nogamycin analogs having a con configuration can be made by utilizing appropriate nucleophilic moieties in a reaction with a compound selected from the group consisting of con 1"β- nogamycin of the presnt invention, nogamycin as known in the prior art, 7-0-alkyl nogamycin and trifluoroacetic acid mixture as outlined by the process herein.

We claim
1. An essentially pure compound having the following structure:

wherein B is a biologically acceptable nucleophile with the proviso that B is not —O—alkyl or —S—alkyl, and T is hydroxyl such that B and T are attached to the ring system of compound I in a con configuration and biologically acceptable acid addition salts thereof.

2. A compound according to claim 1 wherein B is nucleophile from a group consisting of nogalosyl, amino, alkylamino, azido, bis(carbalkoxy)alkyl, alkoxyalkylamino and aminoalkylalkoxy.

3. Con 1"β-nogamycin, a compound according to claim 2, wherein B is nogalosyl.

4. A biologically acceptable acid addition salt of the compound according to claim 3.

5. Con 7-0-acetylnogarol, a compound according to Claim 1, wherein B is acetoxy.

6. A biologically acceptable acid addition salt of the compound according to claim 5.

7. Con 7-Bis(carbethoxy)methyl-7-deoxynogarol, a compound according to claim 2, wherein B is (biscarbethoxy)methyl.

8. A biologically acceptable acid addition salt of the compound according to claim 7.

9. Con 7-(2-methoxyethylamino)-7-deoxynogarol, a compqund according to claim 2, wherein B is 2-methoxyethylamino.

10. A biologically acceptable acid addition salt of the compound according to claim 9.

11. Con-7-methylamino-7-deoxynogarol, a compound according to claim 2, wherein B is methylamino.

12. A biologically acceptable acid addition salt of the compound according to claim 11.

13. Con-7-dimethylamino-7-deoxynogarol, a compound according to claim 2, wherein B is dimethylamino.

14. A biologically acceptable acid addition salt of the compound according to claim 13.

15. Con-7-ethylamino-7-deoxynogarol, a compound according to claim 2, wherein B is ethylamino.

16. A biologically acceptable acid addition salt of the compound according to claim 15.

17. Con-7-diethylamino-7-deoxynogarol. a compound according to claim 2, wherein B is diethylamino.

18. A biologically acceptable acid addition salt of the compound according to claim 17.

19. Con-7-azido-7-deoxynogarol, a compound according to claim 2, wherein B is azido .

20. A biologically acceptable acid addition salt of the compound according to claim 19.

21. Acylates of the Con 7 substituted nogamycin according to claims 3, 5, 7, 9, 11, 13, 15, 17 or 19 wherein said acyl group consists of hydrocarbon carboxylic acid acyl of from 2 to 18 carbon atoms, inclusive: halo-, nitro-, amino-, cyano-, and lower alkoxy-substituted hydrocarbon carboxylic acid acyl of from 2 to 18 carbon atoms, inclusive, and biologically acceptable addition salts thereof.

* * * * *